US012310720B2

(12) United States Patent
Dellimore et al.

(10) Patent No.: US 12,310,720 B2
(45) Date of Patent: May 27, 2025

(54) SWEAT SENSING SYSTEM (71) Applicant: KONINKLIJKE PHILIPS N.V., Eindhoven (NL)

(72) Inventors: Kiran Hamilton J. Dellimore, Utrecht (NL); Eduard Gerard Marie Pelssers, Panningen (NL); Mark Thomas Johnson, Arendonk (BE); Lutz Christian Gerhardt, Eindhoven (NL); Ron Martinus Laurentius Van Lieshout, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 804 days.

(21) Appl. No.: 17/441,055

(22) PCT Filed: Mar. 9, 2020

(86) PCT No.: PCT/EP2020/056132
§ 371 (c)(1),
(2) Date: Sep. 20, 2021

(87) PCT Pub. No.: WO2020/187614
PCT Pub. Date: Sep. 24, 2020

(65) Prior Publication Data
US 2022/0211304 A1 Jul. 7, 2022

(30) Foreign Application Priority Data
Mar. 18, 2019 (EP) ..................................... 19163374

(51) Int. Cl.
*A61B 5/145* (2006.01)
*A61B 5/00* (2006.01)

(52) U.S. Cl.
CPC ........ *A61B 5/14517* (2013.01); *A61B 5/0051* (2013.01); *A61B 5/6833* (2013.01)

(58) Field of Classification Search
CPC . A61B 5/0051; A61B 5/14517; A61B 5/4266; A61B 5/6833; A61B 2010/0009; A61B 10/0064
See application file for complete search history.

(56) References Cited

U.S. PATENT DOCUMENTS 5,518,179 A * 5/1996 Humberstone ..... B05B 17/0684
239/102.2
10,993,657 B1 * 5/2021 Miller .................... A61B 5/681
(Continued)

FOREIGN PATENT DOCUMENTS

| WO | 2009025698 A1 | 2/2009 |
| WO | 2015091171 A1 | 6/2015 |
| WO | 2015091227 A1 | 6/2015 |

OTHER PUBLICATIONS

International Search Report and Written Opinion, International Application No. PCT/EP2020/056132, Mailed on May 8, 2020.
(Continued)

Primary Examiner — Charles A Marmor, II
Assistant Examiner — Andrew E Hoffpauir (57) ABSTRACT A sweat sensing system comprises a mesh for location over a sweat surface on which sweat is formed or collected, and a vibration system for vibrating the mesh to nebulize sweat droplets. The nebulized sweat droplets are condensed on a sensing surface, and a sweat sensor performs biomarker sensing of the sweat at the sensing surface.

20 Claims, 4 Drawing Sheets

(56) References Cited

U.S. PATENT DOCUMENTS

| | | | |
|---|---|---|---|
| 2007/0027383 A1 | 2/2007 | Peyser | |
| 2007/0140041 A1 | 6/2007 | Barrow et al. | |
| 2011/0275918 A1* | 11/2011 | Yamashita | A61B 5/1495 604/93.01 |
| 2012/0149126 A1 | 6/2012 | Cooper et al. | |
| 2013/0074613 A1* | 3/2013 | Jeon | G01N 1/34 73/864 |
| 2013/0079605 A1* | 3/2013 | Bandaru | A61B 5/1486 600/347 |
| 2017/0095233 A1* | 4/2017 | Heikenfeld | A61B 5/6833 |
| 2017/0321177 A1* | 11/2017 | Weitz | C12M 47/04 |
| 2018/0064377 A1* | 3/2018 | Rogers | B01L 3/5027 |
| 2018/0249935 A1* | 9/2018 | Rao | C12Q 1/54 |
| 2018/0353748 A1* | 12/2018 | Heikenfeld | A61B 5/14532 |
| 2019/0000357 A1 | 1/2019 | Ross | |
| 2019/0069818 A1* | 3/2019 | Prasad | A61B 5/14517 |

OTHER PUBLICATIONS

Mena-Bravo, A. et al., "Sweat: a sample with limited present applications and promising future in metabolomics", J Pharm Biomed Anal, Mar. 2014;90:139-47. doi: 10.1016/j.jpba.2013.10.048. Epub Dec. 10, 2013.

Gao, W. et al., "Fully integrated wearable sensor arrays for multiplexed in situ perspiration analysis", Nature. Author manuscript; available in PMC Jan. 28, 2017.

Luo et al., "Acoustic Wave Based Microfluidics and Lab-on-a-Chip", Intech, 2013.

Achim Wixforth, "Acoustically driven planar microfluidics", Superlattices and Microstructures 33 (2003) 389-396.

Z. Sonner, E. Wilder, J. Heikenfeld, G. Kasting, F. Beyette, D. Swaile, F. Sherman, J. Joyce, J. Hagen, N. Kelley-Loughnane, and R. Naik. The microfluidics of the eccrine sweat gland, including biomarker partitioning, transport, and biosensing implications. Biomicrofluidics 9, 031301 (2015).

K. Sato, W. H. Kang, K. Saga, and K. T. Sato, "Biology of sweat glands and their disorders. I. Normal sweat gland function," J. Am. Acad. Dermatol. 20, 537-563 (1989).

N. De Giovanni and N. Fucci, "The current status of sweat testing for drugs of abuse: A review," Curr. Med. Chem. 20, 545-561 (2013).

SCRAM continuous alcohol monitoring product, Accessed Sep. 20, 2021, https://www.scramsystems.com/.

Wescor Nanoduct Neonatal sweat analysis system, Westcor Inc., 2006.

Bandodkar, A. J. et al. Epidermal tattoo potentiometric sodium sensors with wireless signal transduction for continuous non-invasive sweat monitoring. Biosens. Bioelectron. 54, 603-609 (2014).

Rose, D. P. et al. Adhesive RFID sensor patch for monitoring of sweat electrolytes. IEEE Trans. Biomed. Eng. 62, 1457-1465 (2015).

T. Guinovart, G. Valdes-Ramirez, J. R. Windmiller, F. J. Andrade, and J. Wang, "Bandage-based wearable potentiometric sensor for monitoring wound pH," Electroanalysis 26, 1345-1353 (2014).

Bandodkar, A. J. & Wang, J., "Non-invasive wearable electrochemical sensors: a review", Trends Biotechnol. 32, 363-371 (2014).

Carvalho TC, McConville JT. The function and performance of aqueous aerosol devices for inhalation therapy. J Pharm Pharmacol. May 2016;68(5):556-78.

Johnson RE, Sargent F. The Physical and chemical properties of human sweat in confined spaces and factors affecting the water balance. NASA TN Accession No. N6637208, 1966.

Jonsson et al. Modeling the High-Frequency Complex Modulus of Silicone Rubber Using Standing Lamb Waves and an Inverse Finite Element Method, IEEE Transactions on Ultrasonics, Ferroelectrics, and Frequency Control, vol. 61, No. 12, Dec. 2014.

Golsahi et al. Pharm Res. Sep. 2015; 32(9): 3007-3017.

Holbrook et al. J Aerosol Sci. Oct. 1, 2015; 88: 35-47.

* cited by examiner

SWEAT SENSING SYSTEM

This application is the U.S. National Phase application under 35 U.S.C. § 371 of International Application No. PCT/EP2020/056132, filed on 9 Mar. 2020, which claims the benefit of European Application Serial No. 19163374.2, filed 18 Mar. 2019. These applications are hereby incorporated by reference herein.

FIELD OF THE INVENTION

This invention relates to a sweat sensing system, for example for monitoring biomarkers in sweat.

BACKGROUND OF THE INVENTION

Non-invasive, semi-continuous and prolonged monitoring of biomarkers that indicate disease/health status and wellbeing is in demand for monitoring, for example, dehydration, stress, sleep, children's health and in perioperative monitoring.

Sweat, tear fluid and saliva may all be obtained non-invasively. Sweat is a particularly accessible bio fluid, and is a rich source of information relating to the physiology and metabolism of a subject.

Continuous monitoring of high-risk patients, such as those with serious chronic conditions, pre- or post-operative patients, and the elderly, using sweat biomarker monitoring devices can provide higher quality diagnostic information than regular biomarker spot checks as normally done by repeatedly drawing multiple blood samples. Such continuous monitoring may be in a hospital setting or elsewhere.

Human sweat alone or as mixture with sebum lipids may be an easily accessible source for biomarker measurements in wearable on-skin devices.

Some general examples of clinically relevant components of sweat are Na+, Cl− and/or K+ to monitor dehydration, lactate as an early warning for inflammation (which is relevant to sepsis), glucose for diabetics and neonates, and cortisol in relation to sleep apnea and stress monitoring.

More specific examples of biomarkers that can be detected in eccrine/apocrine sweat using suitable capture species (antibodies, aptamers, molecular imprint polymers, etc.) are small molecules such as urea, creatinine, cholesterol, triglycerides, steroid hormones (cortisol), glucose, melatonin; peptides and proteins incl. cytokines such as IL-1alpha, IL-1beta, IL-6, TNF alpha, IL-8 and TGF-beta IL-6, Cysteine proteinases, DNAse I, lysozyme, Zn-α2-glycoprotein, cysteine-rich secretory protein-3 and dermcidin; and large biomarkers such as the Hepatitis C virus.

For instance, cholesterol is an important biomarker associated with elevated risk in development of cardiovascular diseases. Inflammatory markers or cytokines, such as interleukins (e.g. TNF-a, IL-6) play an important role in the immune response and detection or disease monitoring of joint damage in rheumatoid and psoriatic arthritis, and bowel disease.

The development of reliable sweat sensing has, however, been hampered by several issues, in spite of clinical work showing promising results as early as the 1940s and 1950s. To date the impactful application of sweat analysis has been limited mainly to cystic fibrosis diagnostics, and drug and alcohol abuse testing.

As summarized by Mena-Bravo and de Castro in "Sweat: A sample with limited present applications and promising future in metabolomics" J. Pharm. Biomed. Anal. 90, 139-147 (2014), it has been found that the results from sweat sensing can be highly variable, and a correlation between values determined from blood and sweat samples appears to be lacking for various biomarkers. However, historical studies in this area have involved relatively crude sampling techniques, such as collecting large sweat volumes in bags or textiles. Deficiencies in such techniques may have been a contributing factor to this apparent lack of correlation.

Efforts have been made to address these issues by bringing wearable sensors into nearly immediate contact with sweat as it emerges from the skin. A very recent example is the wearable patch presented by Gao et al. in "Fully integrated wearable sensor arrays for multiplexed in situ perspiration analysis" Nature 529, 509-514 (2016). The patch includes a sensor array for measuring Na+, K+, glucose, lactate, and skin temperature. However, the focus of this study is on the development and the integration of the sensors themselves which, whilst evidently crucial, does not address issues relating to sweat sample collection.

The latter is mostly done by placing a several $cm^2$ sized absorbent pad between the skin and the sensor. The assumption is that, providing ample sweat is produced (hence tests are always done on individuals that heavily exercise), the pad will absorb the sweat for analysis, and newly generated sweat will refill the pad and 'rinse away' the old sweat. It is, however, likely that the time-dependent response of the sensor does not directly reflect the actual level of biomarkers over time because of accumulation effects. The sample collection and presentation to the published sensors may not be well-controlled so that continuous reliable sensing over a long period of time is difficult. Such patches may also not be designed to handle the tiny amounts of sweat that are produced under normal conditions, i.e. in the order of nanoliters per minute per sweat gland.

Thus, improvements are required to existing devices for continuous or intermittent monitoring. The detection of biomarkers or analytes in the bio fluid of interest tends to require the device to include a sensor unit having a surface on which capture species are immobilized, which capture species bind the biomarker.

Access to sweat is limited and uneven especially for individuals at rest in a non-thermal neutral state (i.e., outside the thermal neutral zone in which the core body temperature remains very stable and there is no reason to induce sweat production for cooling down the body; typically, 25-30° C. for a naked person at rest or 13-22° C. for a clothed individual) who have sweat rates as low as ~0.03-0.10 nL/min/gland.

There remain problems of biomarker sensing of very small volumes of sweat of the order of nL/min/gland. The filling time of microfluidic devices is then long and there is a substantial time delay between the sweat excretion to the skin and actual measurement, which can be as much as several hours of delay.

SUMMARY OF THE INVENTION

The invention is defined by the independent claims. The dependent claims define advantageous embodiments.

According to examples in accordance with an aspect of the invention, there is provided a sweat sensing system, comprising:

- a mesh for location over a sweat surface on which sweat is formed or collected, having a set of mesh openings;
- a vibration system for vibrating the mesh to provide oscillation adapted to nebulize sweat droplets;
- a condensing unit for condensing the nebulized sweat droplets on a sensing surface; and a sweat sensor for biomarker sensing of the sweat at the sensing surface.

This system enables sensing of small volumes of sweat by performing nebulizing of the sweat from a surface, and condensing the nebulized droplets at a sensing surface. By this approach, much smaller volumes of sweat can be processed, so that biomarker monitoring becomes possible for subjects who are not undertaking physical exercise, such as when working in an office. The analysis of the sensed samples may be semi-continuous by having a continuous collection of sequential samples. Alternatively, sensing data may be collected for subsequent analysis. The system may be used to provide a fast transport of nebulized sweat so that a concentration of biomarkers can be detected in small aliquots of sweat without substantial time delay.

The vibration frequency is selected to provide the creation of an aerosol but without significant heating and evaporation. In particular, evaporation is undesirable since the droplets are to include all of the sweat biomarkers, including biomarkers which can evaporate such as volatile organic components (alcohols, aldehydes, aliphatics, aromatics, carboxylic acids, esters and ketones).

The vibration system is for example for vibrating the mesh to provide oscillation in a frequency range 20 kHz to 2 MHz. This is a preferred range of frequencies, which for example generates particles with a size (diameter) in the range 2 to 90 μm.

The condensing unit for example comprises a set of one or more chimney arrangements.

These direct the nebulized flow to the location where the sweat sensor is located. For example, there may be a chimney arrangement over each mesh opening or more preferably over a respective set of mesh openings, or even a single chimney over the entire mesh.

The chimney arrangements for example each comprise a U-shaped channel. In this way, the collected sweat does not return back down its original path, but can instead be collected after the sensing at a different location.

The chimney arrangements may each comprise at least one hydrophobic channel and at least one hydrophilic channel, with the sensing surface in a hydrophilic channel. In this way, the condensed sweat may be separated from air bubbles and other hydrophobic sweat components such as sebum.

The system may further comprise a discharge chamber for collecting sweat from the sensing surface after sensing. In this way, a flow is provided from the skin, to the sweat sensor, and to the discharge chamber. This allows continuous operation of the system.

A charging system may be provided for charging the nebulized sweat droplets with a first charge, for charging the sensing surface with an opposite, second charge, and for charging surface regions away from the sensing surface with the first charge.

This assists the condensation of the sample to be sensed at the sweat sensor based on electrostatic attraction and repulsion.

The system is for example formed within a patch for application to the skin. This patch may be used for long term sweat monitoring in an unobtrusive way.

The system may further comprise a dilution reservoir and a fluid delivery system for delivering fluid from the dilution reservoir to the sweat surface. There may be very low volumes of sweat excretion, for example when a subject is at rest, so the dilution provides a greater sample volume which thereby makes the nebulization process faster.

In a first set of examples, the mesh is for location over and in contact with the skin. Thus, in this first set of examples, the system may be a compact arrangement which makes direct contact with the skin.

Each mesh opening or sub-sets of mesh openings for example define a pooling chamber having a volume of 1 nL or less. The mesh thus forms pooling areas, and each may then lead to its own respective sweat sensor.

In a second set of examples, the system further comprises:

a support layer for mounting over the skin and which defines a collection reservoir which comprises the sweat surface, above the skin surface; and a fluid delivery system for delivering sweat from the skin surface to the collection reservoir.

In this second set of examples, the sweat is transported from the skin to a collection reservoir. This reservoir may be only just above the skin surface (by the thickness of the support surface). The purpose is to enable better control of the nebulization function. In particular, the material properties of the sweat surface (the skin in the example above and the support surface in this example) determine the nebulization function. The support surface is for example formed as a material layer which is stiffer than the skin and thereby has different response to the vibration of the mesh at the particular vibration frequency.

The fluid delivery system for example comprise a microchannel arrangement.

The sweat sensor may comprise a capture species immobilized on a surface for binding a target analyte and a detector for detecting the presence of the bound target analyte.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 1 shows in schematic form a sweat sensing system;

FIG. 2 shows a first example of the system in more detail;

FIG. 3 shows the mesh structure in more detail;

FIG. 4 shows a modification to the system of FIG. 2;

FIG. 5 shows a plot of elastic modulus of skin versus frequency for a set of different tests;

FIG. 6 shows a second example of the system with a separate sweat surface over the skin; and FIG. 7 shows an approach for reducing the possibility of clogging of the microfluidic system by sweat constituents and air bubbles.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a sweat sensing system comprises a mesh for location over a sweat surface on which sweat is formed or collected and a vibration system for vibrating the mesh to nebulize sweat droplets. The nebulized sweat droplets are condensed on a sensing surface and a sweat sensor performs biomarker sensing of the sweat at the sensing surface.

Figure 1:
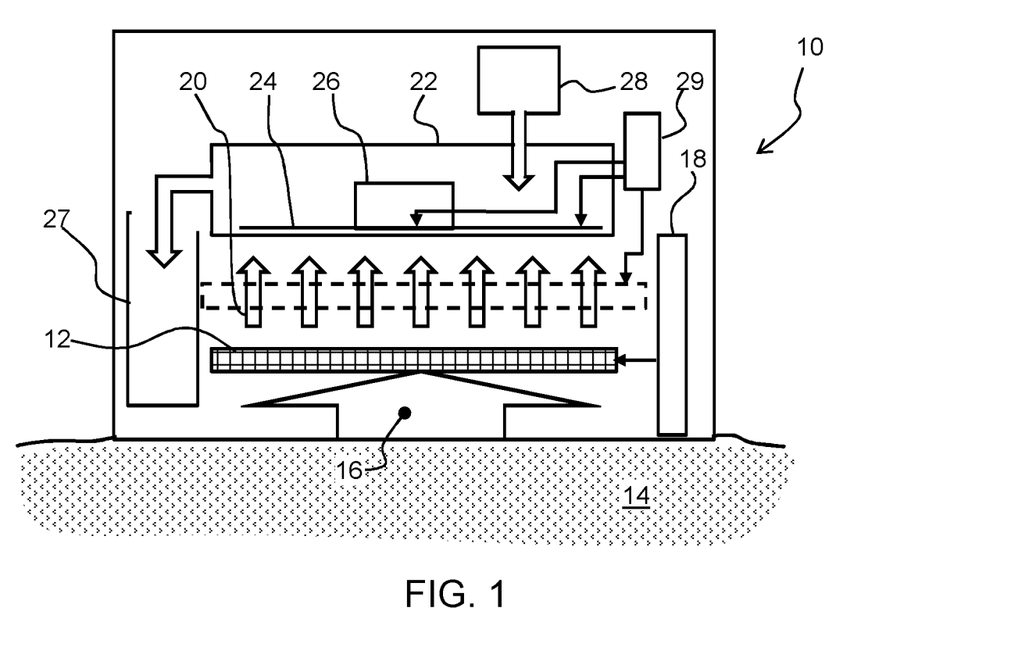

FIG. 1 shows in schematic form the sensing system 10 in the form of a patch for application to the skin.

There is a mesh 12 having a set of mesh openings, the mesh being located over a surface on which sweat is formed or collected. This surface is termed a sweat surface in the following description. It may the skin 14 or it may be a separate surface to which sweat is transported from the skin, as represented schematically by arrow 16.

A vibration system 18 is used for vibrating the mesh to provide oscillation in a frequency range 20 kHz to 2 MHz. This performs nebulization thereby to create sweat droplets. Flows of the sweat droplets are represented by arrows 20. These advance to a condensing unit 22 for condensing the nebulized sweat droplets on a sensing surface 24. A sweat sensor 26 is used for biomarker sensing of the sweat at the sensing surface 24.

The overall system is for example is implemented as a battery-operated patch which is adhered on the skin surface.

The mesh of the nebulizer is adapted and driven to vibrate at these ultrasonic frequencies by a piezo-element, and is arranged with holes arranged to make fine droplets generated through them. The vibration of the mesh causes aerosol generation as the liquid passes through it. The mesh for example comprises a membrane with an array (of for example 1000-7000) laser drilled holes. A mist of very fine droplets is generated through the holes. The holes may form a regular array or an irregular pattern. Mesh nebulizers, and the associated mesh designs, are well known, and this invention may utilize known mesh designs.

As sweat is excreted from a sweat gland onto the skin surface it will pool on the sweat surface (whether the skin itself or a separate surface) until the sweat surface is sufficiently filled to be in contact with the vibrating mesh. The vibrating mesh then oscillates at an ultrasonic frequency, more preferably in the range of 20 kHz to 2 MHz.

The nebulization creates a mist containing tiny droplets, and is an aerosolization process. The key distinction between aerosolization and vaporization is that in the latter method, water vapor is formed which contains none of the biomarkers in sweat, except volatile organic compounds (e.g., ethanol). In contrast, in aerosolization a colloidal suspension of sweat droplets (containing the biomarkers of interest) and gas (in particular air) is formed. The sweat aerosol formed will be rapidly transported to the condensing unit 22, where it will condense and collect for sensing (and optionally also additional real time analysis) by the sweat sensor.

The sweat may be transported by the momentum gained during nebulization, or there may be transport and flow control based on inductively charging the aerosol particles, and using an electric field to induce particle movement.

This approach enables fast and semi-continuous sensing of biomarkers in sweat. Due to the low volume of sweat, the aerosol droplets will adhere to the condenser surface without falling off, which can be further ensured by use of a hydrophilic surface coating on the condenser walls.

An additional advantage of sweat nebulization is that it prevents the accumulation of sweat on the skin for extended periods of time which is known to lead to skin irritation. By nebulizing the sweat directly after excretion the sweat will not stay for very long in contact with the skin.

FIG. 1 shows some optional additional features, which are described in further detail below. A first is a discharge chamber 27 for collecting sweat from the sensing surface after sensing. This allows continuous operation of the system.

A second is a dilution reservoir 28 and a fluid delivery system for delivering fluid from the dilution reservoir 28 to the sweat surface. There may be very low volumes of sweat excretion, for example when a subject is at rest, so the dilution provides a greater sample volume.

A third is a charging system 29 for charging the nebulized sweat droplets with a first charge, for charging the sensing surface with an opposite, second charge, and for charging surface regions away from the sensing surface with the first charge. This assists the condensation of the sample to be sensed at the sweat sensor based on electrostatic attraction and repulsion.

Figure 2:
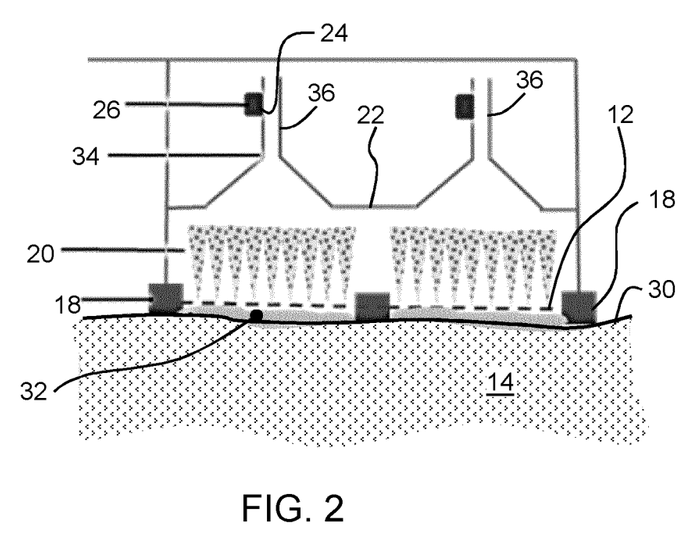

FIG. 2 shows a first example in more detail.

The sweat surface in this example comprises the surface 30 of the skin 14. The mesh 12 is disposed over the skin surface.

The vibration system is shown as a set of vibration sources 18. They may be at the edges only or they may be distributed across the mesh area.

The sweat forms pools 32 over which the mesh is located. The sweat droplet flows 20 lead to the condensing unit 22, which in this example comprises an arrangement of funnels 34. Each funnel 34 has a chimney 36 which defines the sensing surface 24 at which the sweat sensor 26 is located. Each chimney in this example is formed over a sub-array of the openings. This facilitates the manufacture of the chimney arrangement since the scale is then larger than the scale of the openings. There may even be a single chimney for the entire mesh.

The (or each) chimney arrangement has an inner surface which has a funnel part which is adapted to convey the droplets from an associated area of the sweat surface 30 to a smaller channel area. This smaller channel area defines the chimney part. This chimney part leads to a chamber or a sensor surface upstream or downstream of the sensing surface. The funnel part has an inlet end facing or located nearer to the sweat surface and a smaller outlet end facing away from the sweat surface.

A microchannel system and reservoir (not shown in FIG. 2, but shown as 27 in FIG. 1) is provided for removal and storage of waste sweat after it has been sensed by the sweat sensor.

The microchannel system may simply use capillary forces to provide the transport of the waste sweat.

Figure 3:
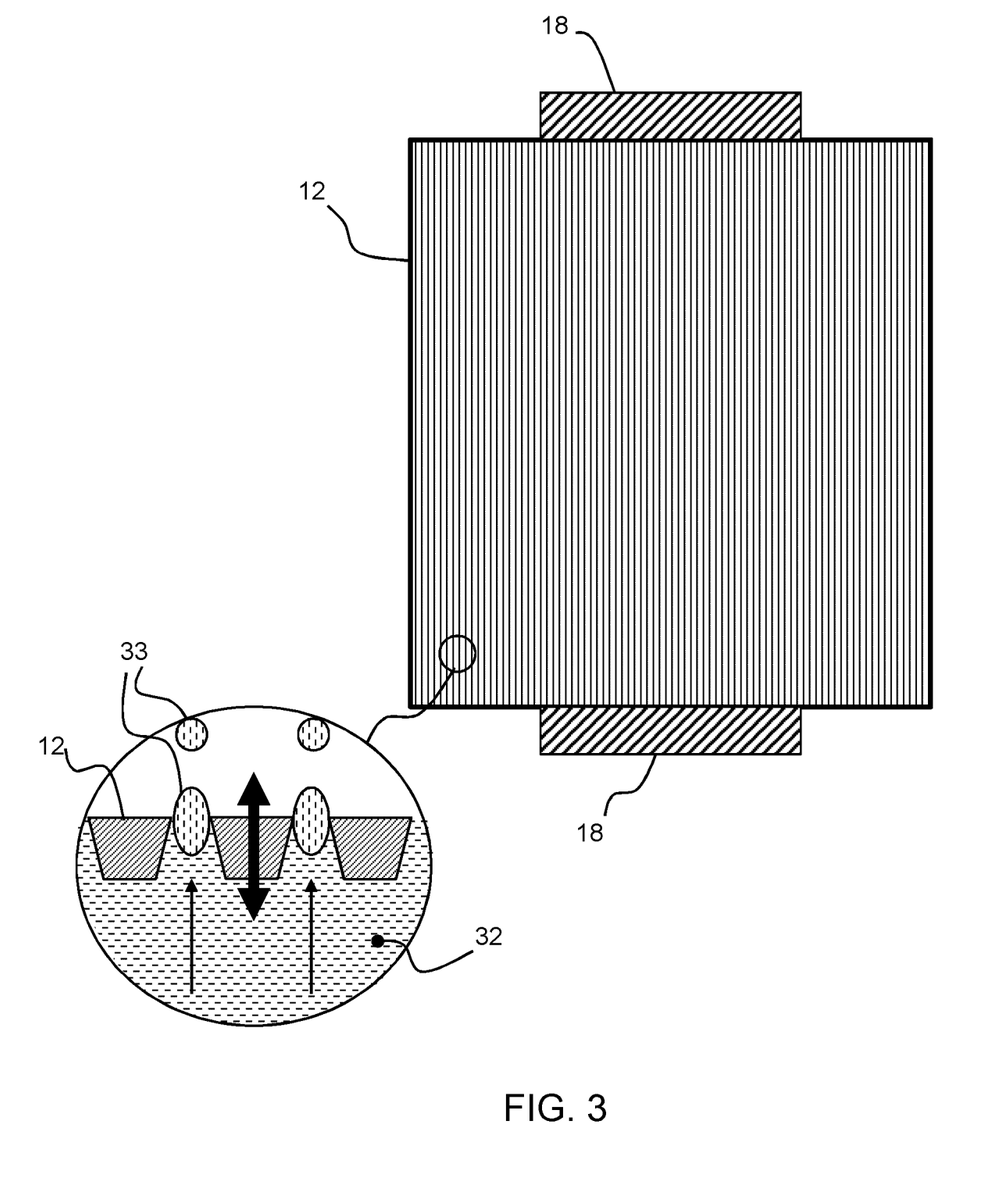

FIG. 3 shows one example of the mesh and vibration source structure in more detail. The vibration source comprises a pair of transducers 18 on opposite sides of the mesh 12. The mesh defines an array of orifices as shown in the enlarged portion. The vibration of the mesh 12, perpendicular to the plane of the mesh as shown by the arrow, causes the pooled sweat 32 to form aerosol droplets 33.

The openings defined by the mesh may be holes or rectangular slits or indeed other shaped openings. The openings for example have a maximum dimension (e.g. diameter for a circular orifice) in the range 10 to 150 μm, for example 20 to 150 µm. The overall mesh has a size of the order of centimeters, such as a maximum dimension of 2 to 20 cm.

Figure 4:
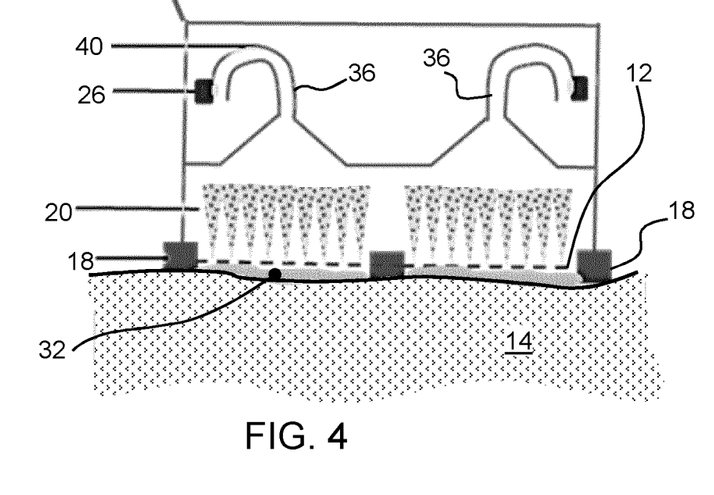

FIG. 4 shows a modification in which each chimney 36 has a U-shaped channel 40 so that the sensed sweat flows automatically to a collection reservoir rather than flowing back to the sweat surface.

The sweat excreted onto the skin surface will be pooled in several small-volume pooling chambers which will enable sufficient sweat to accumulate quickly and fill the pooling chamber such that the sweat makes contact with the vibrating mesh element.

Suitable vibrating meshes are known in the art of nebulization. The oscillation frequency (preferably 20 kHz to 2 MHz) is sufficient to aerosolize the sweat into droplets of the order of 2-90 µm in diameter, depending on the ultrasonic frequency utilized. For example, at 1.4 MHz, 5-7 µm droplets are typically produced, while at 20 kHz droplets on the order of 90 µm are formed.

Using known power consumption values for aerosol generators (e.g., 2 W to obtain an output aerosol rate of 0.2 mL/min) a power of about 10 mW is needed to generate aerosols from small sweat volumes (0.5-1 µL). Such a power requirement can be met through standard flat button batteries suitable for on-body wearable devices.

In order for ultrasonic nebulization to be effective, the viscosity of the liquid needs to be less than approximately 2 mPa·s. Sweat, which is 99% water, easily meets this requirement by having a viscosity in the range of 0.91-0.93 mPa·s.

The skin surface needs to provide a significantly rigid/stiff and un-damped support to enable the effective nebulization of sweat by the ultrasonic vibrating mesh. Excessive damping would prevent the formation of standing waves which are essential to the formation of aerosols by vibrating meshes. Skin is viscoelastic and is known to exhibit non-linear behavior depending on the conditions and constraints to which it is subjected. These conditions include, for example, when skin is stretched vs. relaxed, wet vs. dry, warm vs. cool, etc.

In addition, factors such as age, gender and anatomical location also greatly influence the viscoelastic properties of skin. Of key importance is the dynamic elastic modulus (Young's modulus) of skin when it is exposed to a driving frequency in the ultrasonic range. Experiments have shown that at frequencies above 500 Hz, skin has an elastic modulus greater than 2000 N/m.

Figure 5:
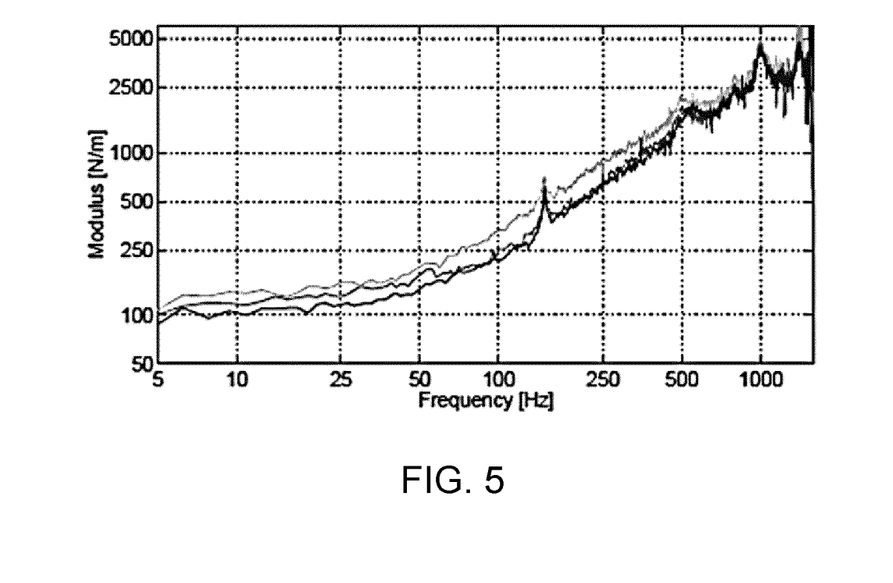

FIG. 5 shows a plot of elastic modulus versus frequency for a set of different skin tests. This shows that skin behaves stiffly in the frequency range of interest.

Thus, investigations have demonstrated that it is possible to use the skin surface as the sweat surface against which the vibrating mesh is positioned.

It is also possible use a separate surface as a reservoir for collection of sweat before the nebulization.

Figure 6:
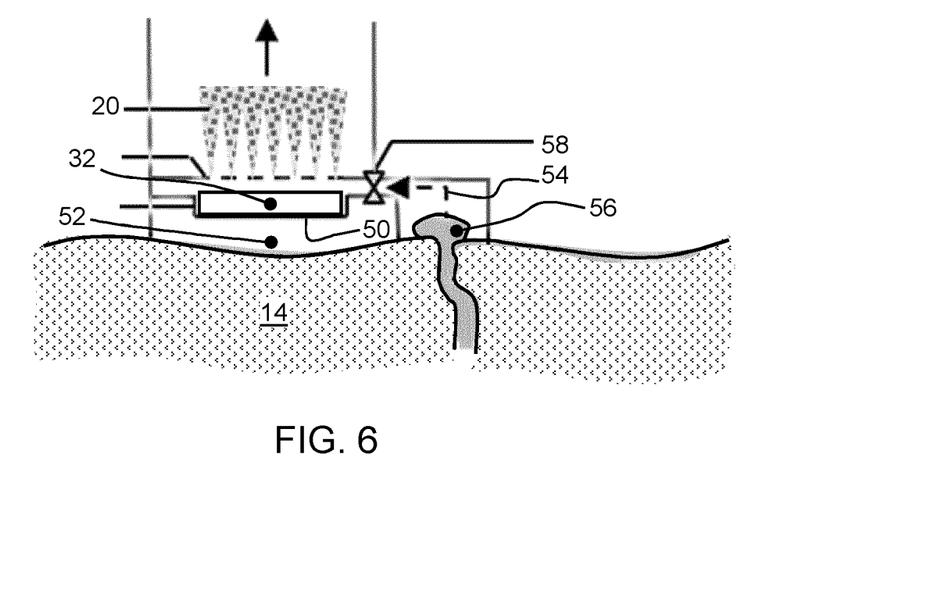

FIG. 6 shows an example with a separate sweat surface 50. The sweat surface 50 is a surface of a support layer 52 and it forms a collection reservoir. A fluid delivery system 54 is provided for delivering sweat 56 from the skin surface to the collection reservoir. The fluid delivery system 54 comprises a microchannel arrangement, for example for transporting the generated sweat by capillary forces. There may be a valve arrangement 58 to provide a sampling function.

Thus, the term "sweat surface" is used to denote the surface at which sweat is formed or else a separate surface on which sweat is collected. In FIG. 2, the sweat surface is the skin i.e. where sweat is formed, and in FIG. 6, the sweat surface is a separate reservoir, i.e. where sweat is collected downstream of the skin.

This arrangement enables more optimal and efficient nebulization of sweat to be achieved. The collection reservoir is not in direct contact with the skin, but is separated from the skin by the support layer 52 which is a semi-stiff material layer (e.g., stiffness >5000 N/m). The microchannel arrangement 54 has channels linked to inlets which open directly onto the sweat glands on the skin surface.

The support layer 52 ensures effective nebulization of the sweat by providing a surface which does not dampen the acoustic standing waves generated by the ultrasonic vibrating mesh.

Note that for simplicity the condensing unit and sweat sensor are not shown. They may have the same design as in FIGS. 2 and 4.

As explained above, the system is for sensing of very small sweat volumes for analysis. The analysis may be part of the sensing, or it may be based on additional subsequent processing of the collected sensing data. A known small volume of "inert" carrier liquid (such as water) may be added, from a reservoir, to take up the tiny volume of excreted sweat and to ensure that there is sufficient liquid to permit semi-continuous nebulization. This is the dilution reservoir 28 shown in FIG. 1. This is of interest in situations in which very small volumes of sweat, for example as low as 0.01-0.03 nl/min/gland, need to be nebulized. These sweat volumes are typical for individuals at rest. As long as the detection limit of the concentration sensor is low enough, the dilution by the carrier liquid is acceptable.

It is also possible to use condensed water vapor captured from Trans Epidermal Water Loss (TEWL) from the skin as the carrier liquid. This would eliminate the problem of carrier liquid depletion over the lifetime of use of the sweat monitoring patch. TEWL occurs via the continuous diffusion of gaseous water vapor from the skin surface (stratum corneum). This water vapor can be captured by using a hollow chamber, which covers part of the skin surface. The water vapor diffuses through the air into the chamber and then condenses on the roof of the chamber, and it can then be captured in a reservoir.

For a patch with an operating time of three days, assuming a carrier fluid flow rate of 30 nL/min and an average sweat flow rate of 52 nL/min, about 225 microliter (=225 mm³) of carrier fluid is needed. In the case of using TEWL as the carrier fluid the marker can be added to the carrier liquid by elution over time.

Figure 7:
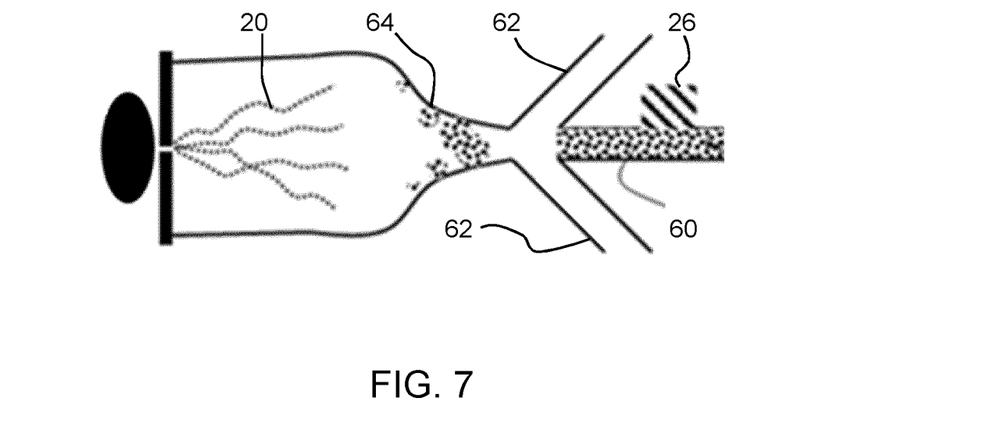

FIG. 7 shows an approach which may be adopted to reduce the possibility of clogging of the microfluidic system by sweat constituents and air bubbles. The condensation chamber is designed with hydrophilic channels 60 and hydrophobic channels 62. The sweat is condensed in a condensing area 64 and is then drawn through a hydrophilic microchannel towards the biomarker sensor 26 where it can be sensed, while other hydrophobic sweat constituents (e.g., sebum, air bubbles, etc.) will be drawn away from the biomarker sensor towards one or more hydrophobic side channels 62. In so doing the clogging of the microchannel containing the biomarker sensor will be prevented thereby enabling accurate and reliable measurements over the lifetime of the sweat patch.

One of the major problems with low sweat production rates is the relatively large sampling area and collection area in relation to the total volume produced. The nebulizer will enable the fast transport of liquid from the skin to the microfluidic system.

The collection of the mist in the microfluidic system can be made more effective by controlling the mist direction or transporting the mist/condensation inside the microfluidic system.

To control the mist direction, the aerosol may be charged in such a way that the corresponding charge of the unwanted deposition areas repel the aerosol. This is the function of the charging system 29 shown in FIG. 1. One way of charging is with an induction charger. By providing the aerosols with a charge, the deposition can be controlled by coating the unwanted areas with the same charge and coating the wanted areas (such as the inlet of the microfluidic system) with an opposite charge.

Known sweat sensors may be used for the biomarker sensing and analysis.

The detection principle of conventional sensor units for detecting an analyte relies on capture species immobilized on a surface. The capture species may be selected to bind a certain analyte. For example, antibodies may be immobilized on the surface, which antibodies capture a particular antigen; the antigen being the analyte of interest. Thus, when a sample contacts the surface, the capture species may bind the analyte present in the sample. When the analyte is bound to the surface via the capture species, various properties, e.g. optical and mechanical characteristics, of the surface are altered with respect to the analyte-free surface. This means that the bound analyte may be detected, determined or assessed using a suitable detector. The detection process may include monitoring a change in the surface resulting from binding of the analyte to the capture species; the change being related, i.e. proportional, to the concentration of the analyte.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A sweat sensing system, comprising:
a mesh having a first surface for location over a sweat surface on which sweat is formed or collected, the mesh having a set of mesh openings extending through the mesh from the first surface to an opposite second surface of the mesh;
a vibration system for vibrating the mesh to provide oscillation adapted to nebulize sweat droplets such that the sweat entering the openings in first surface of the mesh is expelled as nebulized sweat droplets from the second surface of the mesh;
a condensing unit located over the second surface of the mesh for condensing the nebulized sweat droplets onto a sensing surface; and
a sweat sensor for biomarker sensing of the sweat condensed onto the sensing surface.

2. The system as claimed in claim 1, wherein the vibration system is for vibrating the mesh to provide oscillation in a frequency range 20 kHz to 2 MHz.

3. The system as claimed in claim 1, wherein the condensing unit comprises a set of one or more chimney arrangements located over the second surface of the mesh.

4. The system as claimed in claim 3, wherein the chimney arrangements each comprise a funnel having a wide opening facing the second surface of the mesh and a narrow opening feeding a proximal end of a U-shaped channel, wherein the sweat sensor is located at a distal end of the U-shaped channel.

5. The system as claimed in claim 3, wherein the chimney arrangements each comprise a funnel having a wide opening facing the second surface of the mesh and a narrow opening feeding a set of at least one hydrophobic channel and at least one hydrophilic channel, with the sensing surface in a hydrophilic channel.

6. The system as claimed in claim 1, further comprising a discharge chamber for collecting sweat from the sensing surface after sensing.

7. The system as claimed in claim 1, further comprising a charging system for charging the nebulized sweat droplets with a first charge, for charging the sensing surface with an opposite, second charge, and for charging surface regions away from the sensing surface with the first charge.

8. The system as claimed in claim 1, further comprising a dilution reservoir and a fluid delivery system for delivering fluid from the dilution reservoir to the sweat surface.

9. The system as claimed in claim 1, wherein the mesh is for location over and in contact with the skin.

10. The system as claimed in claim 9, wherein each mesh opening or a sub-set of mesh openings define a pooling chamber having a volume of 1 nL or less.

11. The system as claimed in claim 1, further comprising:
a support layer for mounting over the skin and which defines a collection reservoir which comprises the sweat surface, above the skin surface; and
a fluid delivery system for delivering sweat from the skin surface to the collection reservoir.

12. The system as claimed in claim 11, wherein the fluid delivery system comprises a microchannel arrangement.

13. The system as claimed in claim 1, wherein the sweat sensor comprises a capture species immobilized on a surface for binding a target analyte and a detector for detecting the presence of the bound target analyte.

14. The system as claimed in claim 1, wherein the system is formed as a patch for application to the skin.

15. A sweat sensing system, comprising:
a mesh having a first surface for location over a sweat surface on which sweat is formed or collected, the mesh having a set of mesh openings extending through the mesh from the first surface to an opposite second surface of the mesh;
a piezo-element for vibrating the mesh to provide oscillation adapted to nebulize sweat droplets such that the sweat entering the set of mesh openings in the first surface of the mesh is expelled as nebulized sweat droplets from the second surface of the mesh;
at least one funnel having a wide opening facing the second surface of the mesh and configured to receive the nebulized sweat droplets, and a narrow opening feeding at least one channel, the at least one channel configured to condense the nebulized sweat droplets onto a sensing surface; and a biomarker sweat sensor operatively contacting the sensing surface.

16. The system as claimed in claim 15, wherein the piezo-element is configured to vibrate the mesh to provide oscillation in a frequency range 20 kHz to 2 MHz.

17. The system as claimed in claim 15, comprising a plurality of funnels and a plurality of channels, each funnel having a wide opening facing the second surface of the mesh and a narrow opening feeding a respective channel.

18. The system as claimed in claim 17, wherein the biomarker sensor is one of a plurality of biomarker sweat sensors of the system, wherein each channel is a U-shaped channel having a proximal end fed by a respective funnel of the plurality of funnels, and a distal end operatively in contact with a respective biomarker sweat sensor of the plurality of biomarker sensors.

19. The system as claimed in claim 17, wherein each channel includes a set of at least one hydrophobic channel and at least one hydrophilic channel, with the sensing surface located in the at least one hydrophilic channel.

20. The system as claimed in claim 15, wherein the system is formed as a patch for application to the skin.

* * * * *